United States Patent [19]

Fox et al.

[11] Patent Number: 5,674,220

[45] Date of Patent: Oct. 7, 1997

[54] BIPOLAR ELECTROSURGICAL CLAMPING DEVICE

[75] Inventors: William D. Fox, New Richmond; David C. Yates, West Chester, both of Ohio

[73] Assignee: Ethicon Endo-Surgery, Inc., Cincinnati, Ohio

[21] Appl. No.: 536,726

[22] Filed: Sep. 29, 1995

[51] Int. Cl.$^6$ .................................................. A61B 17/39
[52] U.S. Cl. .............................. 606/51; 606/45; 606/41; 606/205; 606/50
[58] Field of Search .......................... 606/1, 41, 42, 606/45–52, 205–208; 128/751

[56] References Cited

U.S. PATENT DOCUMENTS

| | | | |
|---|---|---|---|
| 2,068,721 | 1/1937 | Wappler et al. | 606/51 |
| 4,375,218 | 3/1983 | DiGeronimo . | |
| 4,655,216 | 4/1987 | Tischer | 606/51 |
| 4,938,761 | 7/1990 | Ensslin . | |
| 5,403,312 | 4/1995 | Yates et al. | 606/46 |
| 5,443,463 | 8/1995 | Stern et al. | 606/52 |
| 5,445,638 | 8/1995 | Rydell et al. . | |
| 5,458,598 | 10/1995 | Feinberg et al. | 606/52 |
| 5,482,054 | 1/1996 | Slater et al. | 606/46 |
| 5,489,292 | 2/1996 | Tovey et al. | 606/205 |
| 5,509,922 | 4/1996 | Aranyi et al. | 606/46 |
| 5,558,100 | 9/1996 | Cox | 606/52 |

FOREIGN PATENT DOCUMENTS

| | | |
|---|---|---|
| 2355-521 | 6/1976 | France . |
| WO 95/15124 | 6/1995 | WIPO . |

*Primary Examiner*—Lee S. Cohen
*Assistant Examiner*—Michael Peffley
*Attorney, Agent, or Firm*—Bernard E. Shay

[57] ABSTRACT

An electrosurgical hemostatic instrument is provided in which the coagulation status of tissue engaged by two elements delivering an electrosurgical energy to tissue may be observed, and in which damage from thermal spread may be minimized. A preferred embodiment of the invention provides a bipolar endoscopic clamping, coagulation and cutting device. In this device, the outer conductive surface of the tissue engaging elements includes openings therethrough. The openings are adapted to allow an observer to see the tissue as it is being treated, coagulation may be observed by watching the region through the openings. In addition, the inclusion of openings in the end effector enhances coagulation from speed by reducing the thermal mass of the end effector without substantially reducing the structural strength of the end effector jaws. Finally, the openings may be used to observe the motion of the knife as it moves through the end effector.

2 Claims, 5 Drawing Sheets

BIPOLAR ELECTROSURGICAL CLAMPING DEVICE

FIELD OF THE INVENTION

The present invention relates to an electrosurgical hemostatic grasping, clamping or forceps type device, and in particular, to a clamping and cutting device including a pair of electrically conductive clamping elements with openings in the clamping elements.

BACKGROUND OF THE INVENTION

Electrosurgical hemostatic devices have been used for effecting improved hemostasis by heating tissue and blood vessels to cause coagulation or cauterization. Monopolar electrosurgical devices utilize one active electrode associated with the cutting or cauterizing instrument and a remote return or ground electrode which is usually attached externally to the patient. Thus in surgery utilizing monopolar instruments, electrical current passes from the active electrode, through the patient to the return electrode.

In bipolar electrosurgical instruments both electrodes are included on the instrument and, generally, both electrodes are active. Thus, a typical bipolar instrument includes two or more electrodes which are charged to different electrical potentials. In bipolar instruments, the coagulating current flows through tissue positioned between the electrodes.

Bipolar forceps, being one type of bipolar electrosurgical instrument, have been used in various procedures for coagulating tissue. Generally bipolar forceps include two opposing jaws each connected to an output electrode of an electrical generator such that the opposing jaws are charged to different electrical potentials. Organic tissue being electrically conductive, when the jaws are used to grasp tissue the two electrodes apply electrical current through the grasped tissue. The use of bipolar forceps may, in certain circumstances, cause areas of thermal spread, i.e., regions of coagulation caused by the dissipation of heat outside the area defined by the grasping or engaging surfaces of the forceps.

U.S. application Ser. No. 08/095,797 filed on Jun. 22, 1993, illustrates, in a preferred embodiment, a clamping and coagulating device in which most of the tissue being treated by the end effector of the device is not visible to the user. The electrodes in the preferred embodiment of this device are offset from each other with respect to the tissue grasping surfaces so that the likelihood of arcing or shorting is reduced. However, in this device it is difficult to visualize coagulation as it is occurring to the tissue unless thermal spread is occurring.

U.S. application Ser. No. 08/415,957 filed on Apr. 3, 1995, illustrates a clamping, cutting and coagulating device in which the tissue being treated by the end effector of the device is partially visible to the user, improving visual feedback. The electrodes of the preferred embodiment of this device are also offset to reduce the likelihood of arcing or shorting.

Electrical energy is used in medical instruments for hemostasis, that is to stop or slow bleeding in tissue. Application of electrical current in conjunction with pressure applied by the end effector results in a significant reduction in bleeding, and may be used to reduce bleeding along a cut line prior to cutting tissue. The electrical current which passes through the tissue acts to heat the tissue. As the tissue is heated, it changes in color and texture. The experienced surgeon may, by looking for changes in the color or texture of the tissue around the end effector, determine when to turn off the current to the end effector. Although the changes in tissue color and texture around the end effector are useful to the surgeon, it is beneficial in many procedures to limit the region effected by the electrical current and insulating heat, i.e. to limit the thermal spread. In addition, it is beneficial in certain circumstances to speed coagulation of tissue clamped by the jaws. Therefore, it would be beneficial to design an end effector wherein the thermal mass of the end effector is reduced to speed coagulation. In addition, it would be beneficial to design an end effector wherein the movement of the knife blade may be observed as the knife moves through the tissue. Further, it would be beneficial to design an end effector wherein tissue grouped by the end effector may be observed as it is treated.

In the device illustrated in FIG. 1, the solid bipolar electrodes make it difficult to observe the tissue as it is treated. As tissue between the electrodes coagulates its impedance rises, and the coagulation current seeks a lower impedance path through the tissue. Tissue which touches uncoated electrodes on the sides of the end effector, offers a low impedance path, increasing thermal spread and decreasing current density in the region between the electrodes. Thus, the surgeon waits until thermal spread is observed to conclude that the tissue between the electrodes is being treated. In the simplified cross-section of an end effector in FIG. 1, first electrode 1 and second electrode 2 hold tissue 3. In the end effector in FIG. 1, electrical current travels along current paths 4 between first electrode 1 which is charged to a first electrical potential and second electrode 2 which is charged to a second electrical potential. As the tissue coagulates, coagulation region 5 forms between electrode 1 and electrode 2 increasing the impedance of the tissue between the electrodes. In the device illustrated in FIG. 1, current paths 4 extend well beyond the edges of the end effector and out into tissue 3. The resulting coagulation region therefore extends laterally out into the tissue around the end effector.

The device illustrated in FIG. 2 utilizes what is known as "compression zone" technology wherein one electrode is positioned inside one jaw of the device and the second electrode is positioned around the outside of at least one jaw. As tissue between the inner and outer electrode coagulates, the coagulated tissue between the jaws insulates the inner electrode, effectively stopping coagulation and thermal spread. In the simplified cross-section of an end effector illustrated in FIG. 2, tissue 13 is positioned between first insulator 16 and second insulator 18. In the end effector of FIG. 2, electrical current flows between first electrode 11 and third electrode 17, in addition, if region 12 is an active electrode current may flow between second electrode 12 and third electrode 17. First electrode 11 and second electrode 12 are charged to a first electrical potential while third electrode 17 is charged to a second electrical potential. As current flows through tissue 13, coagulation regions 15 are formed. The arrangement of electrodes in the end effector of FIG. 2 confines the current paths and thus, coagulation regions 14 to the space between first insulator 16 and second insulator 18.

SUMMARY OF THE INVENTION

A surgical device according to the present invention includes a bipolar coagulation device which may be used to grasp and treat tissue and may further include a cutting element to cut the treated tissue. In one embodiment of the present invention, an end effector of an electrosurgical device includes first and second clamping elements arranged such that tissue may be clamped between the first and second elements. In this embodiment, the clamping elements include at least one opening in the side of the electrode. In a further embodiment of the present invention, multiple openings are arranged in the side of the end effector. In a further embodiment of the present invention, the end effector includes multiple openings in the side of each jaw of the end effector along with a first knife channel in the first clamping surface and a second knife channel in the second clamping surface. In a further embodiment of the present invention, the openings extend into the knife channel.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
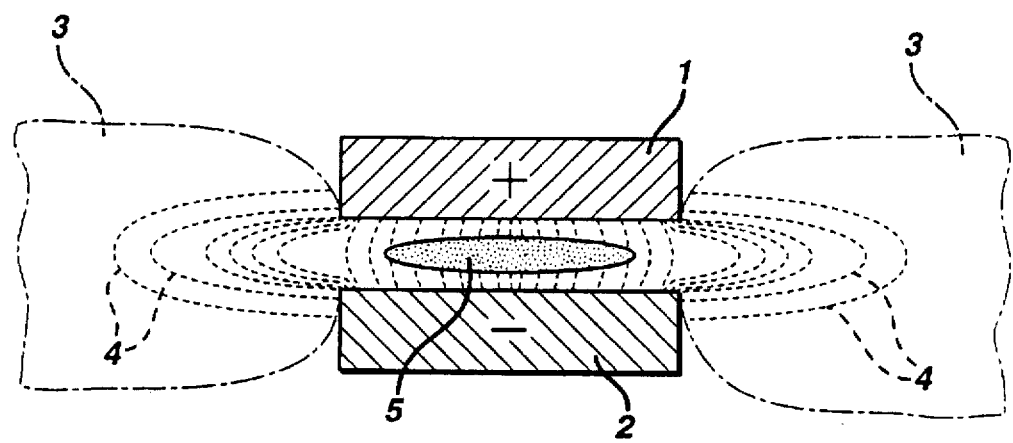
FIG. 1 is a simplified cross-section of a bipolar end effector without external insulation.
Figure 2:
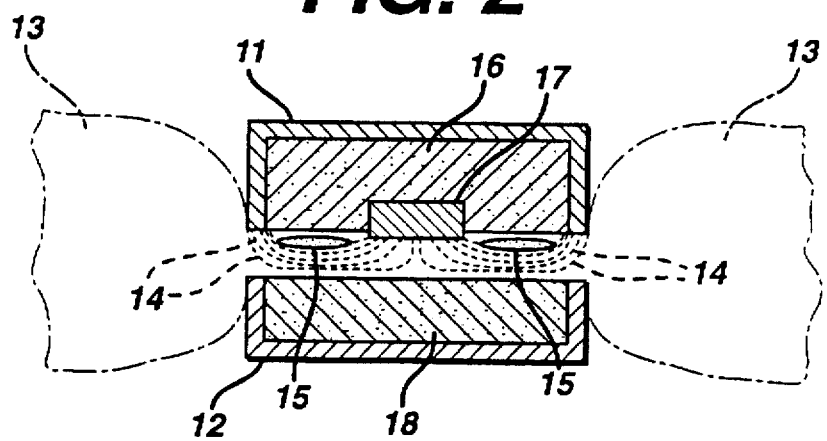
FIG. 2 is a simplified cross-section of a bipolar end effector utilizing compression zone technology.
Figure 3:
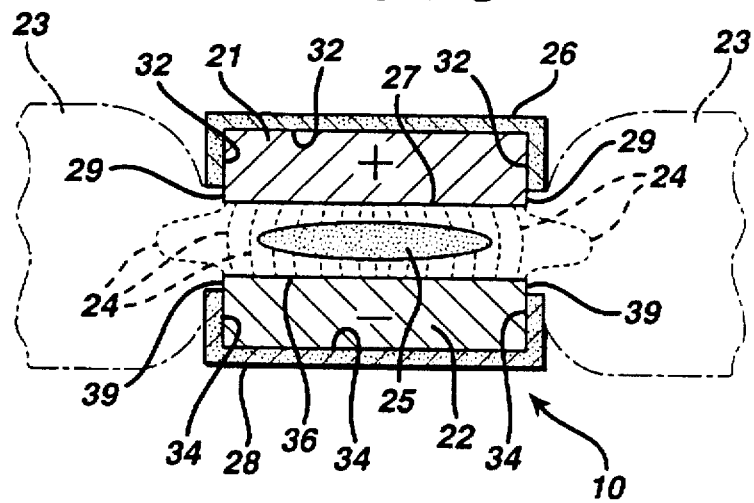
FIG. 3 is simplified cross-section of one embodiment of a bipolar end effector according to the present invention.

In the simplified cross-section of an end effector according to the present invention illustrated in FIG. 3, tissue 23 is grasped between first electrode 21 and second electrode 22. In end effector 10, an electrical potential or voltage is generated between electrode 21 and second electrode 22. Thus when an electrically conductive material such as organic tissue is grasped by the end effector, electrical current flows between first electrode 21 and second electrode 22. In FIG. 3, insulators 26 and 28 cover substantially all of the outer surface of first electrode 21 and second electrode 22 respectively confining a substantial portion of the current path 24 to the region between first electrode 21 and second electrode 22. A small portion of the electrical current flows through tissue 23 in the region outside electrode 21 and electrode 22, coagulating the tissue and providing the surgeon with visible evidence of coagulation. Thus, the coagulated region around the outside of end effector 10 may be refereed to as the feedback region since the thermal spread in this region provides the surgeon with visible evidence of coagulation.

In the embodiment illustrated in FIG. 3, insulation layer 26 covers substantially all of the outer surface 32 of electrode 21, leaving only a small region 29 of outer surface 32 exposed and electrically conductive. Region 29 may be referred to as an outer electrode. Insulation layer 28 covers substantially all of the outer surface 34 of electrode 22, leaving only a small region 39 of outer surface 34 exposed and electrically conductive. In the embodiment illustrated in FIG. 3, outer electrode 29 is located adjacent the interface between outer surface 32 and tissue grasping surface 27. The region adjacent the interface between outer surface 32 and tissue grasping surface 27 may be referred to as the transition region. In the embodiment illustrated in FIG. 3, outer electrode 39 is located adjacent the interface between outer surface 34 and tissue grasping surface 36. The region of outer surface 34 adjacent tissue grasping surface 36 may be referred to as the transition region. More generally, as used herein, the transition region refers to any portion of the jaw around the interface between the outer face of an electrode and the tissue grasping surface. Tissue 23 conducts current between electrodes 21 and 22, generating coagulation region 25. Since insulators 26 and 28 do not cover the entire outer surface 32 and 34 of conductors 21 and 22 respectively, leaving outer electrodes 29 and 39, a small portion of the current will flow outside the region between grasping surfaces 27 and 36, coagulating tissue outside that region and providing visual confirmation of coagulation. The size and shape of the feedback region may be varied by varying the portion of outer surface 32 and 34 which are not covered by insulative coating i.e. by varying the size and location of outer electrodes 29 and 39. Where necessary, shorting may be prevented by, for example, including an island of insulation on the grasping surface 27 or 36 of either electrode 21 or 22 to establish an insulative gap between the conductive surfaces. However, the grasped tissue will generally prevent shorting of the electrodes during treatment and, once the tissue is treated it may not be necessary or desirable to prevent the electrodes from shorting.

Figure 4:
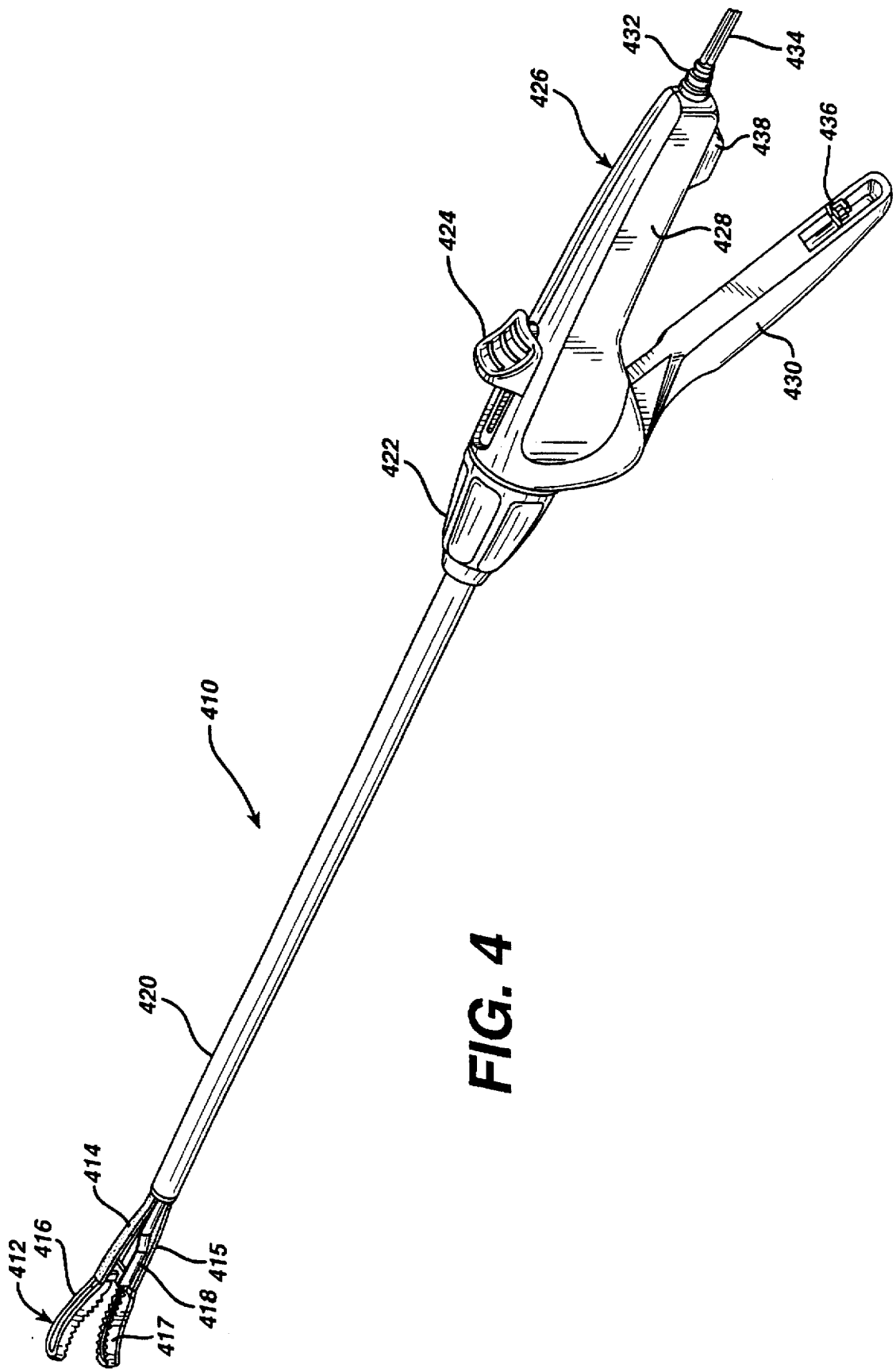
FIG. 4 is an elevated side view of a bipolar clamping, cutting and coagulating device including an end effector according to the present invention.

FIG. 4 is a perspective view of a bipolar forceps 410 according to the present invention. In bipolar forceps 410, upper jaw 416 and lower jaw 417 of end effector 412 are supported by upper wire form 414 and lower wire form 415. Wire forms 414 and 415 also act as conductors supplying bipolar electrical energy to upper jaw 416 and lower jaw 417 respectively. Tissue stop 418 is positioned within closure tube 420. Rotation knob 422 is affixed to closure tube 420 to cause rotation of closure tube 420 with respect to handle 426. Handle 426 includes knife button 424, grip 428 and trigger 430. Electrical cord 434 is connected to handle 426 through strain relief 432. Trigger latch 436 is positioned on trigger 430. Handle latch shield 438 is positioned on grip 428.

Figure 5:
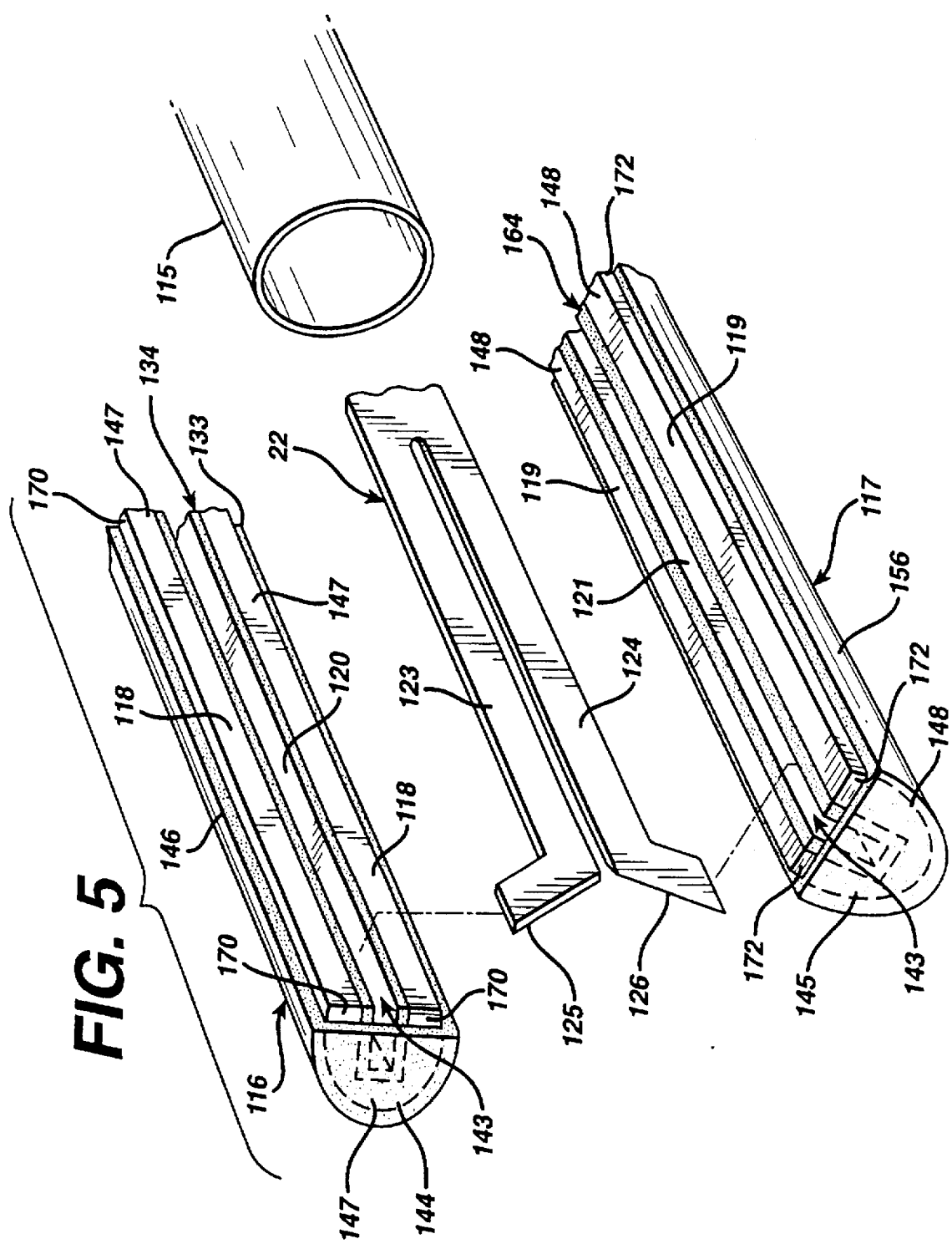
FIG. 5 is a perspective exploded view of one embodiment of a bipolar end effector according to the present invention.

FIG. 5 is an exploded view of one embodiment of a bipolar end effector according to the present invention. As illustrated in FIG. 5, jaw members 116 and 117 include electrodes 147 and 148 respectively, which include tissue grasping surfaces 118 and 119 respectively. Top jaw 116 and bottom jaw 117 are arranged to grasp or position tissue therebetween. Jaw members 116 and 117 include an outer electrically insulative coating 146 and 156 of, for example, a ceramic material. Closure tube 115 is adapted to close the jaws 116 and 117 together as tube 115 is advanced distally. Jaw member 116 includes a U-shaped insulator 134 formed on the inside of electrode 147. Jaw member 117 includes a U-shaped insulator 164 formed on the inside of electrode 148. The upper half 120 of groove or knife channel 143 is lined by insulator 134. The lower half 121 of groove of knife channel 143 is insulated by insulator 164. Insulators 146 and 156 are arranged so that when tissue is grasped and jaws 116 and 117 are closed together, a portion of the external surface of electrodes 147 and 148 is exposed. The exposed portion of the outer surface of electrode 147 forms outer electrode 170. The exposed portion of the outer surface of electrode 148 forms outer electrode 172. Outer electrode 170 is formed in the transition region at the interface between the outer surface of electrode 147 and tissue grasping surface 118 while outer electrode 172 is formed in the transition region at the interface between the outer surface of electrode 148 and tissue grasping surface 119. The size and shape of outer electrodes 170 and 172 may be adjusted by selectively depositing more or less insulation in the transition regions of electrodes 147 and 148 respectively. Control of the size and shape of the feedback region in treated tissue may be achieved, at least in part, by controlling the size and shape of the outer electrodes for example, by controlling the size and shape of outer electrodes 170 and 172. For the purposes of this application, outer electrodes may also be referred to as feedback or thermal spread electrodes. The distal end 144 and 145 of jaw member 116 has an inwardly angled shape. The inwardly angled distal ends 144 and 145 form a V-shaped space at the distal end jaws 116 and 117, which assists in channeling tissue in between jaws 116 and 117.

In FIG. 5, knife 122 is adapted to cut tissue by moving distally in knife channel 143 when jaws 116 and 117 are closed to grip tissue. Knife 122 includes upper knife section 123 and lower knife section 124. Upper knife section 123 includes sharpened blade 125 at the distal end of upper knife section 123. Lower knife section 124 includes sharpened blade 126 at the distal end of the lower knife section 124.

Figure 6:
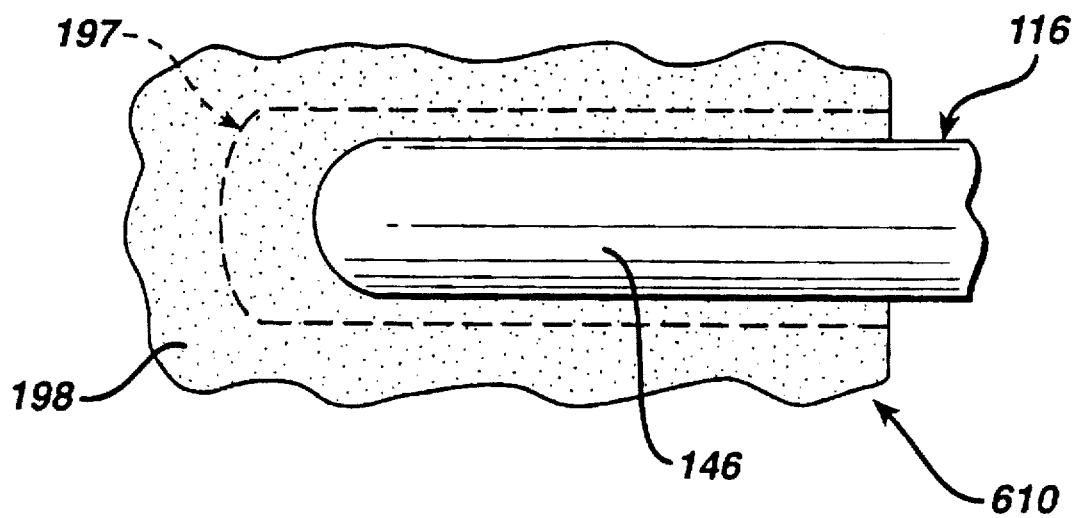
FIG. 6 is a top view of the bipolar end effector illustrated in FIG. 5 as it grasps tissue.

FIG. 6 is a top view of the end effector illustrated in FIG. 5. In FIG. 6, upper jaw 116 of end effector 610 grasps tissue 198. As electrical current flows through the tissue, insulator 146 prevents current from flowing except where the electrode is exposed (e.g. between the tissue grasping electrodes and through the outer electrodes). An area of tissue 197 surrounding the end effector is illustrated in which desiccation of and/or thermal effects on the tissue may be visualized. Region 197 may be referred to as the feedback region.

Figure 7:
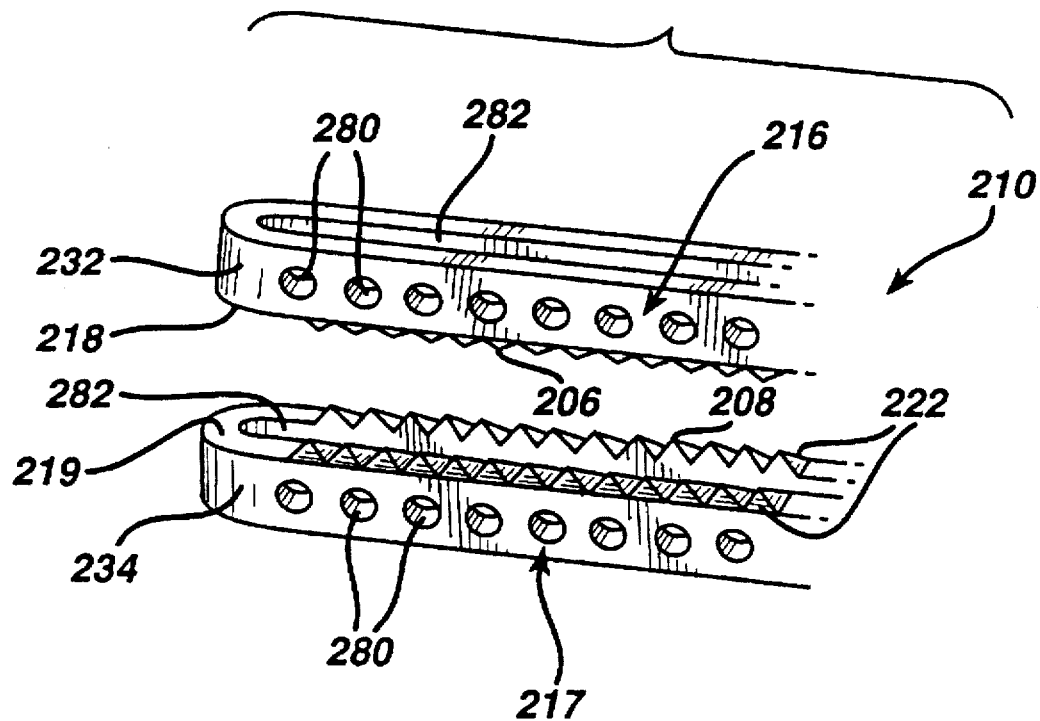
FIG. 7 is a perspective view of a bipolar end effector including openings according to the present invention.

FIG. 7 is a perspective view of a straight bipolar end effector 210 without insulation. End effector 210 comprises upper jaw electrode 216 and lower jaw electrode 217. Electrodes 216 and 217 include tissue grasping teeth 206 and 208 respectively. Tissue grasping teeth 206 are disposed on at least a portion of upper tissue grasping surface 218. Tissue grasping teeth 208 are disposed on at least a portion of lower tissue grasping surface 219. In the embodiments of FIG. 7, grasping teeth 206 and 208 are chamfered such that outer faces 222 slant in toward the center of end effector 210. In other embodiments of the present invention, outer surface faces 222 may have a radius rather than a chamfer. In other embodiments of the present invention, outer faces 222 may be parallel to or a continuation of outer surfaces 232 and 234. In FIG. 7, jaws 216 and 217 include openings 280. Openings 282 are interspersed along the length of jaws 216 and 217. Holes such as holes 280 perform at least three functions in an end effector such as the end effector illustrated in FIG. 7. Openings 280 may be used to observe the tissue clamped between jaws 216 and 217. Alternatively, openings 280 may be used to observe the position of a cutting element, such as the knife illustrated in FIG. 5, as it moves along channel 282 when jaws 216 and 217 are closed. Openings 280 reduce the physical and thermal mass of jaws 216 and 217. Reducing the thermal mass of the jaws reduces the jaws ability to absorb heat generated in the treated tissue, thus increasing coagulation speed which may, in certain circumstances, improve the performance of the end effector. In the embodiment of FIG. 7, U-shaped electrodes 216 and 217 have a substantially rectangular cross section. The use of a substantially rectangular cross section improves the structural strength of the jaws and, as a result, the clamping force which may be applied to the jaws. The rectangular cross section of the jaw improves shielding of a knife blade as it moves along channel 282.

Figure 8:
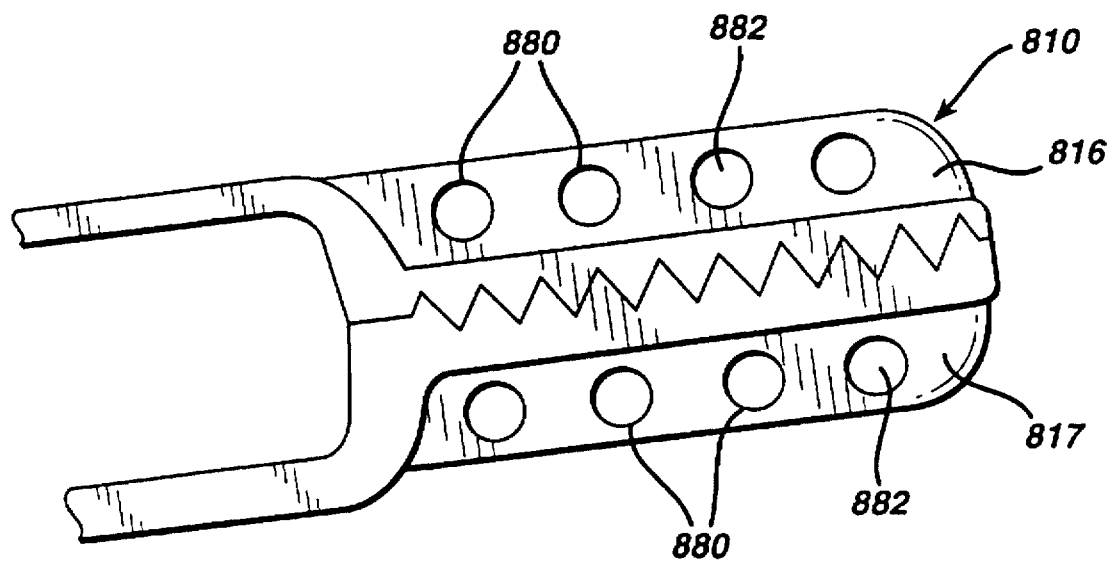
FIG. 8 is a side view of a bipolar end effector including openings according to the present invention.
Figure 9:
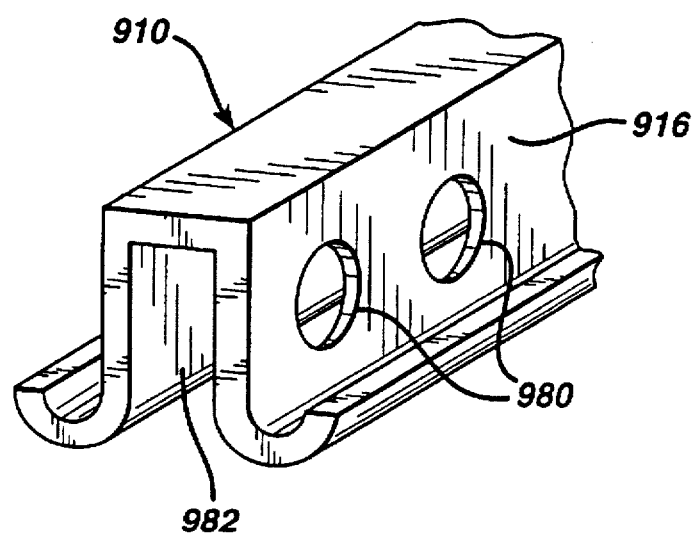
FIG. 9 is a perspective view of a portion of the top jaw of an end effector according to the present invention.

FIG. 8 is a side view of a bipolar end effector 810 including openings 880. In FIG. 8, upper jaw 816 and lower jaw 817 include material covering the knife channel such that the knife motion is only observed through openings 880. FIG. 9 is a perspective view of a portion of a further embodiment of an end effector 910 including openings 980 according to the present invention. In FIGS. 8 and 9, the openings perform multiple functions, including, providing visual access to the knife as it moves through the knife channel 882 and 982 respectively, providing visual access to tissue gripped by the end effector and, by removing material, thus reducing physical and thermal mass of the end effector without compromising the structural integrity of the end effector. The openings in the end effectors illustrated in FIGS. 7–9 are substantially evenly spaced to provide improved visual access and to improve observability at the knife as it travels down the knife channel. Since there may be no need to include openings in certain portions of the end effector, it may not be desirable to have all of the openings evenly spaced.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, while all of the embodiments illustrated and described herein include round openings, one skilled in the art would recognize that openings of any shape including square, rectangular, oblong or any other shape would fall within the scope of applicants invention. Accordingly, it is intended that the invention be limited only by the spirit and scope of the appended claims.

What is claimed is:

1. A bipolar electrosurgical instrument comprising.

an end effector located at a distal end of the instrument, said end effector comprising:

first tissue grasping element including an exterior surface, a channel therethrough and a plurality of openings through said exterior surface to said channel; and second tissue element including an exterior surface, a channel therethrough and a plurality of openings through said exterior surface to said channel; and a cutting element operatively coupled to said electrosurgical instrument and adapted to move through said channels and arranged to cut tissue positioned between said first and second tissue grasping surfaces.

2. A bipolar electrosurgical instrument comprising:

an end effector located at the distal end of the instrument said end effector comprising:

first tissue grasping element including a plurality of openings in an exterior surface of said time element wherein said plurality of openings are arranged to connect said first exterior surface to a channel in said end effector;

second tissue grasping element including a plurality of openings in an exterior surface of said second element wherein said plurality of openings are arranged to connect said second exterior surfaces to a channel in said end effector; and a knife operatively coupled to said electrosurgical instrument and adapted to move within said channel and arranged to cut tissue positioned between said first and second tissue grasping elements.

* * * * *